United States Patent [19]
Ulrich et al.

[11] Patent Number: 6,080,782
[45] Date of Patent: Jun. 27, 2000

[54] CYCLOHEXYL DIHYDROBENZOFURANES

[75] Inventors: Wolf-Rüdiger Ulrich; Thomas Martin, both of Constance, Germany

[73] Assignee: BYK Gulden Lomberg Chemische Fabrik GmbH, Constance, Germany

[21] Appl. No.: 08/952,275

[22] PCT Filed: May 14, 1996

[86] PCT No.: PCT/EP96/02055

§ 371 Date: Nov. 18, 1997

§ 102(e) Date: Nov. 18, 1997

[87] PCT Pub. No.: WO96/36626

PCT Pub. Date: Nov. 21, 1996

[30] Foreign Application Priority Data

May 18, 1995 [CH] Switzerland ............... 1471/95
Jan. 22, 1996 [DE] Germany ............... 196 01 911

[51] Int. Cl.$^7$ ............... A01N 43/08; C07D 307/78
[52] U.S. Cl. ............... 514/469; 514/470; 514/826; 514/886; 514/889; 514/914; 549/469
[58] Field of Search ............... 549/469; 514/469, 514/470, 826, 886, 889, 914

[56] References Cited

FOREIGN PATENT DOCUMENTS

| 0 771 794 | 5/1997 | European Pat. Off. . | |
|---|---|---|---|
| WO 93 19747 | 10/1993 | WIPO | 514/469 |
| WO 93 19749 | 10/1993 | WIPO | 514/469 |
| WO 93 19751 | 10/1993 | WIPO | 514/469 |
| WO 9636624 | 11/1996 | WIPO . | |

OTHER PUBLICATIONS

Chem. Abstract vol. 125 No. 114620, Hasegawa et al, "Preparation of (Imidazolyl–Ethyl) Benzofuran Derivatives as 5–Lipoxygenase Inhibitors" 1996.

*Primary Examiner*—John Kight
*Assistant Examiner*—Raymond Covington
*Attorney, Agent, or Firm*—Jacobson, Price, Holman & Stern, PLLC

[57] ABSTRACT

Compounds of formula I are selective cyclic nucleotide phosphodiesterase (PDE) inhibitors (namely of type IV). They and pharmaceutical compositions in which they are active ingredients are useful as bronchial therapeutics, for elimination of erectile dysfunction and for treatment of disorders, particularly those of inflammatory nature. The compounds are distinguished by low toxicity, good enteral absorption (high bioavailability), a great therapeutic breadth and the absence of significant side effects.

12 Claims, No Drawings

6,080,782

CYCLOHEXYL DIHYDROBENZOFURANES

RELATED APPLICATION

This application is related to a concurrently-filed application, Ser. No. 08/952,276 allowed.

TECHNICAL FIELD

This invention relates to novel compounds which are used in the pharmaceutical industry for the production of medicaments.

PRIOR ART

International Patent Application WO92/12961 describes benzamides having PDE-inhibiting properties. International Patent Applications WO93/25517 and WO93/19749 disclose trisubstituted phenyl derivatives as selective PDE IV inhibitors. International Patent Application WO94/02465 describes inhibitors of c-AMP phosphodiesterase and of TNF.

DESCRIPTION OF THE INVENTION

It has now been found that the dihydrobenzofurans described in greater detail below, which differ from the previously published compounds by substitution of a completely different kind, have surprising and particularly advantageous properties.

The invention thus relates to compounds of the formula I (see formula sheet I), in which R1 is 1-6C-alkoxy, 3-7C-cycloalkoxy, 3-7C-cycloalkylmethoxy, benzyloxy or 1-4C-alkoxy which is completely or partially substituted by fluorine, R2 is 1-4C-alkyl and R3 is hydrogen or 1-4C-alkyl, or R2 and R3, together and including the two carbon atoms to which they are bonded, are a 5-, 6- or 7-membered hydrocarbon ring, if desired interrupted by an oxygen atom, R4 is hydrogen, cyano, carboxy, 1-4C-alkoxycarbonyl and nitro and R5 is hydroxy, carboxyl, 1-4C-alkoxycarbonyl, amino, mono- or di-1-4C-alkylamino, 1-4C-alkylcarbonylamino, 1-4C-alkylsulphonylamino, trifluoromethylsulphonylamino or cyanoamino, and their salts.

1-6C-Alkoxy represents a radical which, in addition to the oxygen atom, contains a straight-chain or branched alkyl radical having 1 to 6 carbon atoms. Alkyl radicals having 1 to 6 carbon atoms which may be mentioned here are, for example, the hexyl, isohexyl (2-methylpentyl), neohexyl (2,2-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3-7C-Cycloalkoxy represents, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkylmethoxy represents, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

1-4C-Alkoxy which is completely or partially substituted by fluorine which may be mentioned are, for example, the 1,2,2-trifluoroethoxy, the 2,2,3,3,3-pentrfluoropropoxy, the perfluoroethoxy and in particular the 1,1,2,2-tetrafluoroethoxy, the trifluoromethoxy, the 2,2,2-trifluoroethoxy and the difluoromethoxy radicals.

A 5-, 6- or 7-membered hydrocarbon ring, if desired interrupted by an oxygen atom, which may be mentioned are the cyclopentane, the cyclohexane, the cycloheptane, the tetrahydrofuran and the tetrahydropyran rings. If R2 and R3, together and including the two carbon atoms to which they are bonded, form a 5-, 6- or 7-membered ring, a spiro compound is present.

1-4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1-4C-Alkoxy represents a radical which, in addition to the oxygen atom, contains one of the above-mentioned 1-4C-alkyl radicals. Examples which may be mentioned are the methoxy and the ethoxy radicals.

1-4C-Alkoxycarbonyl represents a carbonyl group to which one of the abovementioned 1-4C-alkoxy radicals is bonded. Examples which may be mentioned are the methoxycarbonyl radical ($CH_3O$—CO—) and the ethoxycarbonyl radical ($CH_3CH_2O$—CO—).

1-4C-Alkylcarbonyl represents a carbonyl group to which one of the abovementioned 1-4C-alkyl radicals is bonded. An example which may be mentioned is the acetyl radical ($CH_3CO$—).

Mono-or di- 1-4C-alkylamino radicals which may be mentioned are, for example, the methylamino, the dimethylamino, the ethylamino, the diethylamino, the propylamino and the isopropylamino radicals.

A 1-4C-alkylcarbonylamino radical which may be mentioned is, for example, the acetylamino radical (—NH—CO—$CH_3$).

1-4C-Alkylsulphonylamino represents a sulphonylamino radical, which is substituted by one of the abovementioned 1-4C-alkyl radicals. An example which may be mentioned is the methylsulphonylamino radical (—NH—$SO_2$—$CH_3$).

Compounds of the formula I to be emphasized are those in which

R1 is 1-4C-alkoxy, 3-5C-cycloalkoxy, 3-5C-cycloalkylmethoxy or 1-4C-alkoxy which is completely or partially substituted by fluorine, R2 is 1-4C-alkyl and R3 is hydrogen or 1-4C-alkyl, or R2 and R3, together and including the two carbon atoms to which they are bonded, are a cyclopentane, cyclohexane, tetrahydrofuran or tetrahydropyran ring, R4 is hydrogen, cyano, carboxyl or 1-2C-alkoxycarbonyl and R5 is hydroxy, carboxyl, 1-2C-alkoxycarbonyl, amino or mono- or di-1-2C-alkylamino, and their salts.

Preferred compounds of the formula I are those in which

R1 is 1-4C-alkoxy, 3-5C-cycloalkoxy or 1-4C-alkoxy which is completely or partially substituted by fluorine, R2 and R3, together and including the two carbon atoms to which they are bonded, are a cyclopentane or cyclohexane ring, R4 is hydrogen, cyano, carboxyl or 1-2C-alkoxycarbonyl and R5 is hydroxy, carboxyl, 1-2C-alkoxycarbonyl, amino or mono- or di-1-2C-alkylamino, and their salts.

Particularly preferred compounds of the formula I are those in which

R1 is methoxy,

R2 and R3, together and including the two carbon atoms to which they are bonded, are a cyclopentane ring, R4 is hydrogen or cyano and R5 is hydroxyl or carboxyl, and their salts.

Suitable salts for compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, where the acids are employed in salt preparation—depending on whether a mono-or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can be initially obtained, for example, as process products in the preparation of the compounds according to the invention on an industrial scale, are converted into pharmacologically tolerable salts by processes known to the person skilled in the art.

The compounds of the formula I can be present as cis or trans isomers and—if the substitions —R2 and —CH$_2$R3 are not identical—are also chiral compounds. The invention therefore includes both all pure diastereomers and pure enantiomers and their mixtures in any mixing ratio including the racemaies.

The enantiomers can be separated in a manner known per se (for example by preparation and separation of corresponding diastereoisomeric compounds).

The invention further relates to a process for the preparation of the compounds of the formula I and their salts. The process is characterized in that a) compounds of the formula II (see formula sheet I), in which R1, R2, R3 and R4 have the meanings indicated above and Z is an oxygen atom (O), are reacted under conditions which, if desired, selectively reduce the carbonyl group or in that b) for the preparation of compounds of the formula I in which R1, R2, R3 and R4 have the meanings indicated above and R5 is a carboxyl group, corresponding compounds of the formula II in which Z is the group C(Br)$_2$ are hydrolysed and in that If desired, compounds of the formula I obtained are then converted into their salts, or in that salts of the compounds of the formula I obtained are converted into the free compounds.

If desired, further compounds of the formula I can also be converted into other compounds of the formula I in a manner known to the person skilled in the art by derivatization (in particular of the radicals R4 and R5).

The substances according to the invention are isolated and purified in a manner known per se, e.g. by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a non-solvent for the addition salt or by evaporating the solvent. Salts obtained can be converted by alkalization or by acidifying into the free compounds, which in turn can be converted into salts. In this manner, pharmacologically non-tolerable salts can be converted into pharmacologically tolerable salts.

The reduction of the carbonyl group in compounds of the formula II according to variant a) is carried out in a manner known to the person skilled in the art, preferably in suitable inert solvents such as 1,2-dimethoxyethane or an alcohol such as methanol, using a suitable reducing agent, such as, for example, sodium borohydride or lithium borohydride.

The hydrolysis of compounds of the formula II according to variant b), in which Z is the group C(Br)$_2$, is carried out by use of the methods known to the person skilled in the art, e.g. as described in the following examples.

Compounds of the formula II in which R1, R2 and R3 have the abovementioned meanings, R4 is hydrogen and Z is oxygen (O) can be prepared by selective hydrogenation of the carbon double bond in the cyclohexene ring of corresponding compounds of the formula III (see formula sheet I).

Compounds of the formula II in which R1, R2, R3 and R4 have the abovementioned meanings and Z is the group C(Br)$_2$ are obtained, for example, by reaction of corresponding compounds of the formula II in which Z is oxygen (O) with carbon tetrabromide and triphenylphosphane in a manner known to the person skilled in the art.

Compounds of the formula II in which R1, R2 and R3 have the abovementioned meanings, R4 is cyano and Z is oxygen (O), can be prepared by use of methods known to the person skilled in the art, starting from corresponding compounds of the formula IV (see formula sheet I) in which X is the group —C(O)—OCH$_3$, according to the general reaction scheme on the formula sheet II. The reaction sequence is described by way of example under "starting compounds"; the preparation of further compounds can be carried out analogously.

Compounds of the formula III in which R1, R2 and R3 have the abovementioned meanings are accessible, for example, by addition of appropriate compounds of the formula IV, in which X has the meaning lithium, to 1,4-cyclohexanedione and subsequent elimination of water. Expediently, the 1,4-cyclohexanedione is employed in partially protected form, for example as a monoethylene ketal, and the protective group is removed again after reaction has taken place.

Compounds of the formula IV in which X is lithium are accessible from corresponding compounds of the formula IV in which X is halogen, in particular bromine, by metal-halogen exchange.

The compounds of the formula IV in which R1, R2 and R3 have the abovementioned meanings and X is halogen or the group —C(O)—OCH$_3$ can be prepared according to the general reaction scheme on the formula sheet IIa. The synthesis of compounds of the formula IV is described by way of example under "starting compounds". Further compounds of the formula IV can be prepared in an analogous manner.

The following examples illustrate the invention in greater detail without restricting it. The abbreviation h stands for hour(s), min for minute(s), RT for room temperature, m.p. for melting point, DMSO for dimethyl sulphoxide, DMF for dimethylformamide, THF for tetrahydrofuran, Pd(DIPHOS)$_2$ for bis[bis(1,2-diphenylphoshino)ethane] palladium(0). PEG-400 for polyethylene glycol 400 and TLC for thin-layer chromatography.

EXAMPLES

Final Products

1. Cis- and Trans-4-Cyano-4-(2,3-dihydro-7-methoxybenzofuran-2-spiro-1'-cyclopentan-4-yl)-1-cyclohexanol 1.1 Cis-4-Cyano-4-(2,3-dihydro-7-methoxybenzofuran-2-spiro-1'-cyclopentan-4-yl)-1-cyclohexanol Sodium borohydride (2.0 g, 52.4 mmol) is introduced into absolute methanol (70 ml) with stirring at RT. A suspension of the compound prepared according to A1 (6.3 g, 19.4 mmol) in absolute methanol (130 ml) is then added dropwise. After fresh addition of sodiumborohydride (1.4 g, 36.7 mmol), the reaction mixture is treated with 2N hydrochloric acid until a pH of 2 is achieved. A saturated sodium chloride solution (300 ml) and distilled water (100 ml) are added to the reaction solution and it is extracted with ethyl acetate (100 ml, 3 times). The combined organic phases are dried over magnesium sulphate and concentrated in vacuo after filtration. After flash chromatography on silica gel [petroleum ether/ethyl acetate 6:4], the title compound (2.8 g) is obtained as a colourless solid. [TLC, petroleum ether/ethyl acetate (6:4), R$_f$=0.20], m.p. 143° C.

1.2 Trans-4-Cyano-4-(2,3-dihydro-7-methoxybenzofuran-2-spiro-1'-cyclopentan-4-yl)-1-cyclohexanol The trans-hydroxy compound was obtained from the same batch as a colourless solid (0.75 g). [TLC, petroleum ether/ethyl acetate (6:4), R$_f$=0.37], m.p. 145° C.

2. Cis-4-(2,3-Dihydro-7-methoxybenzofuran-2-spiro-1'-cyclopentan-4-yl)-1-cyclohexanol 0.05 g (1.3 mmol) of sodium borohydride is added to a solution of 0.11 g (0.36 mmol) of the compound prepared according to B1 in 10 ml of 1,2-dimethoxyethane and the mixture is stirred for 12 h at RT. The mixture is then treated with 5 ml of 2N hydrochloric acid, 50 ml of distilled water and 100 ml of ethyl ether, the aqueous phase is separated off from the organic phase and reextracted with ethyl acetate, and the organic phases are dried over sodium sulphate and evaporated in a rotary evaporator. Column chromatography affords 47 mg of the title compound as a viscous wax. [TLC (nanoplates, petroleum ether/ethyl acetate, 6:4), R$_f$=0.23]

3. Cis-4-(2,3-Dihydro-7-methoxybenzofuran-2-spiro-1'-cyclopentan-4-yl)-1-cyclohexanecarboxylic acid 10 ml of 10N sodium hydroxide solution are added to 10 ml of PEG-400 and the mixture is stirred under nitrogen at RT for ½ h. After addition of 0.1 g of Pd(DIPHOS)$_2$ in 3 ml of absolute methylene chloride and 3 ml of PEG-400, the mixture is stirred at RT for a further 2 h under nitrogen, during which the solution turns black. A solution of 1.1. g (2.4 mmol) of the compound prepared according to C1 in 5 ml of absolute methylene chloride and 5 ml of PEG-400 is then added dropwise and the mixture is stirred at 60° C. for 20 h. After cooling the reaction solution, it is acidified with 6N hydrochloric acid to pH=2, and the aqueous phase is separated off from the organic phase and extracted again by shaking with 2×100 ml of ethyl acetate. The organic phases are combined, dried over sodium sulphate and concentrated to dryness and the residue is purified by column chromatography and by subsequent recrystallization from ether. 0.31 g of the title compound is obtained as a white solid of m.p. 103–105° C.

Starting Compounds

A1. 4-Cyano-4-(2,3-dihydro-7-methoxybenzofuran-2-spiro-1'-cyclopentan-4-yl)cyclohexanone 0.6 g (1.56 mmol) of the compound prepared according to A2 is dissolved in a mixture of 1 ml of DMSO, 1 ml of distilled water and 0.5 g of sodium chloride and the mixture is stirred at 180–185° for 10 h. After cooling the mixture, 200 ml of distilled water are added to the reaction solution and it is extracted with ethyl acetate, and the organic phase is separated off, dried over sodium sulphate and evaporated to dryness. After flash chromatography, 0.4 g of the title compound results as a yellowish solid of m.p. 92–94° C.

A2. Methyl 5-cyano-5-(2,3-dihydro-7-methoxybenzofuran-2-spiro-1'-cyclopentan-4-yl)-2-oxocyclohexanecarboxylate 0.25 g (0.82 mmol) of sodium hydride (80% strength in paraffin) is added in portions at RT under nitrogen to a solution of 1.2 g (0.29 mmol) of the compound prepared according to A3 in 25 ml of 1,2-dimethoxyethane, and the mixture is refluxed for 6 h, then allowed to cool to RT and stirred at RT for a further 48 h. 5 ml of methanol and 10 ml of 1N hydrochloric acid are subsequently added, then the mixture is treated with 100 ml of distilled water and extracted with ethyl acetate. The organic phases are combined, dried over sodium sulphate and evaporated to dryness. By means of column chromatography, 0.6 g of the title compound is obtained as a white solid of m.p. 137–139° C.

A3. Methyl 4-cyano-4-(2,3-dihydro-7-methoxybenzofuran-2-spiro-1'-cyclopentan-4-yl)heptane-1,7-dicarboxylate A solution of 1.5 g (0.67 mmol) of the compound prepared according to A4 and 1 ml of Triton B in 50 ml of absolute acetonitrile is heated at 60° C. for 10 min and 6 ml (0.66 mmol) of methyl acrylate are subsequently added dropwise at this temperature. The solution is heated to reflux for 6 h. After cooling, the solvent is stripped off in a rotary evaporator, the residue is taken up in 150 ml of ethyl ether and the mixture is extracted by shaking with half-saturated sodium chloride solution. The organic phase is dried and stripped off in a rotary evaporator. Column chromatography affords 2.0 g of the title compound as a yellow oil [TLC (petroleum ether/ethyl acetate 6:4) $R_f=0.55$].

A4. 2,3-Dihydro-7-methoxybenzofuran-2-spiro-1'-cyclopentan-4-yl-acetonitrile 2.4 g (0.01 mol) of the compound prepared according to A5 are dissolved in 50 ml of absolute toluene and treated with stirring with 1 ml of fresh thionyl chloride. The mixture is refluxed for 1 h. After cooling to RT, the solvent is stripped off. The residue is then coevaporated a further 3 times together with 50 ml of toluene in each case. The residue is taken up in 30 ml of absolute toluene and slowly added dropwise at RT to a suspension of 0.5 g (0.01 mol) of sodium cyanide in 20 ml of absolute DMF and 1 ml of 15-crown-6. The mixture is stirred at RT for 4 h. and then added to 200 ml of half-saturated sodium chloride solution and extracted with 200 ml of ethyl acetate. The organic phases are combined and dried over sodium sulphate. After flash chromatography, 1.9 g of the title compound are obtained as a brown oil. [TLC (petroleum ether/ethyl acetate 6:4) $R_f$0.83].

A5. 2,3-Dihydro-7-methoxybenzofuran-2-spiro-1'-cyclopentan-4-yl)methanol 1.8 ml (6.0 mmol) of sodium dihydrido-bis(2-methoxyethoxy)aluminate (SDMA) are added under nitrogen to 15 ml of toluene. 1.6 g (6.0 mmol) of the compound obtained according to A6 are dissolved in 10 ml of toluene and slowly added dropwise under a continuous stream of nitrogen to the SDMA solution. After everything has been added dropwise, the mixture is stirred for a further 30 min at RT and the solvent is then stripped off in the rotary evaporator. 10 ml of distilled water are added to the residue and the mixture is extracted with 200 ml of ethyl acetate. The organic phases are combined, dried and evaporated. 1.2 g of a pale yellow oil are obtained, which by addition of n-pentane spontaneously begins to crystalize. [TLC (petroleum ether/ethyl acetate 6:4)$R_f=0.34$].

A6. Methyl 2,3-dihydro-7-methoxybenzofuran-2-spiro-1'-cyclopentane-4-carboxylate 10.2 g of the compound prepared according to A7 are dissolved in 500 ml of anhydrous n-hexane and treated with about 5 g of Amberlyst 15. The mixture is stirred at RT for 3 days, filtered and concentrated. The residue is chromatographed on a silica gel column using ethyl acetate/petroleum ether (4:6), and the chromatographically pure fractions are combined, concentrated and dried in a high vacuum, 7.2 g of the title compound are obtained as a yellow oil.

A7. Methyl-2-cyclopenten-1-ylmethyl-3-hydroxy-4-methoxybenzoate 12.7 g of the compound prepared according to A8 are treated with 50 ml of quinoline and the mixture is stirred at 190° C. for 1 h. After cooling, it is treated with water, a pH of 3 is set using 2N hydrochloric acid and the mixture is extracted with ethyl acetate. The residue which remains after concentrating the solvent is chromatographed on a silica gel column using ethyl acetate/petroleum ether (4:6). The chromatographically pure fractions are concentrated and dried in a high vacuum, 10.2 g of the title compound are obtained as a yellow oil.

A8. Methyl 3-(2-methylenecyclopentyloxy)-4-methoxybenzoate 28.5 g of methyltriphenylphosphonium bromide are suspended in 300 ml of anhydrous THF under nitrogen and the mixture is cooled to −40° C. 50 ml. of n-butyllithium (1.6 mol) in n-hexane are then added dropwise with stirring. After stirring at −20 to −10° C. for 30 min, a solution of 20 g of the compound prepared according to A9 in 100 ml of abs. THF is added dropwise. The mixture is then allowed to warm to RT and is stirred for a further 1 h. It is poured onto water and extracted with ethyl acetate. The oil remaining after concentrating the organic phase is chromatographed on a silica gel column using ethyl acetate/petroleum ether (4:6). The chromatographically pure fractions are combined, concentrated and dried in a high vacuum. 12.7 g of the title compound are obtained as a colourless oil.

A9. Methyl 4-methoxy-3-(2-oxocyclopentyloxy)benzoate 23.8 g of methyl 3-hydroxy-4-methoxybenzoate are dissolved in 200 ml of anhydrous DMF and the solution is treated with 35 g of potassium carbonate (ground) and 13 ml of 2-chlorocyclopentanone. The mixture is stirred at 60° C. for 3 h, then the solid is filtered off with suction and the filtrate is concentrated in vacuo. The residue is chromatographed on a silica gel column using ethyl acetate/petroleum ether (4:6). The chromatographically pure fractions are combined, concentrated and dried in a high vacuum. 24.3 g of the title compound are obtained as a pale yellow oil.

B1. 4-(2,3-Dihydro-7-methoxybenzofuran-2-spiro-1'-cyclopentan-4-yl)cyclohexanone 4.0 g (0.013 mol) of the compound obtained according to B2 are dissolved in 300 ml of ethanol, treated with 0.3 g of 10% strength Pd/C and hydrogenated in a recirculating hydrogenation apparatus for 1 h. After filtering off and washing the catalyst with methanol, the organic phase is stripped off in the rotary evaporator and the residue is purified by means of column chromatography. 3.8 g of the title compound are obtained as a clear oil [TLC (nanoplates, petroleum ether/ethyl acetate, 6:4) $R_f=0.43$].

B2. 4-(2,3-Dihydro-7-methoxybenzofuran-2-spiro-1'-cyclopentan-4-yl)cyclohex-3-en-1-one 50 ml of distilled water and 2 spatula tipfuls of p-toluenesulphonic acid monohydrate are added to a solution of 7.6 g (0.021 mol) of the compound prepared according to B3 in 100 ml of toluene and the mixture is heated to reflux for 2 h. After cooling, the organic phase is stripped off in the rotary evaporator, the residue is taken up in 100 ml of acetone and a spatula tipful of p-toluenesulphonic acid is added. After the mixture has refluxed for 8 h, it is allowed to cool, the acetone is stripped off, the residue is taken up in ether, the solution is treated with 100 ml of 1N sodium hydroxide solution, and the organic phase is separated off and extracted with ether. After combining and drying the organic phases over sodium sulphate, the solution is concentrated and the product is purified by column chromatography. 5.4 g of the title compound are obtained as a yellow oil. [TLC (nanoplates, petroleum ether/ethyl acetate, 6:4) $R_f=0.41$].

B3. 4-Hydroxy-4-(2,3-dihydro-7-methoxybenzofuran-2-spiro-1'-cyclopentan-4-yl)cyclohexanone monoethylene ketal 21.2 ml (0.036 mol) of n-butyllithium are added dropwise at −89° C. under nitrogen to a solution of 9.5 g (0.034 mol) of the compound prepared according to B4 in 100 ml of absolute THF and the mixture is stirred at this temperature for a further 30 min. A solution of 5.3 g (0.34 mol) of cyclohexanedione monoethylene ketal is then added dropwise at −78° C. and the mixture is then stirred at −70° C. for a further 2 h. After warming to RT, it is treated with 100 ml of distilled water and neutralized with 1N hydrochloric acid. The aqueous phase is separated off from the organic phase and is additionally extracted with methylene chloride. The organic phases are combined and dried over sodium sulphate, evaporated in a rotary evaporator and purified by means of column chromatography. 7.1 g of the title compound are obtained as a yellow oil. [TLC (petroleum ether/ethyl acetate, 6:4) $R_f$=0.16].

B4. 4-Bromo-2,3-dihydro-7-methoxybenzofuran-2-spiro-1'-cyclopentane 9.0 g of Amberlist 15 are added to a solution of 8.4 g (0.03 mol) of the compound prepared according to B5 in 100 ml of absolute toluene and the mixture is stirred at 100° C. for 10 h. After cooling the mixture, the H+ ion exchanger is filtered off and washed with 100 ml of methanol. After stripping off the organic phase and column chromatography, 7.4 g of the title compound are obtained as a yellow oil [TLC (petroleum ether/ethyl acetate, 6:4) $R_f$ 0.72].

B5. 2-Cyclopent-1-enylmethyl-3-hydroxy-4-methoxybromobenzene 52.1 ml (0.082 mol) of n-butyllithium are added dropwise under nitrogen at −89° C. to a suspension of 26.5 g (0.074 mol) of methyltriphenylphosphonium bromide in 200 ml of absolute THF. The suspension is then warmed to −30° C., during which the suspension goes into solution. After renewed cooling to −70° C., a solution of 19.2 g (0.067 mol) of the compound prepared according to B6 in 200 ml of absolute THF is added dropwise under nitrogen. The mixture is then warmed to −10° C. and stirred at this temperature for 5 h. [TLC (petroleum ether/ethyl acetate, 6:4) $R_f$ (methylene compound)=0.81]. After warming to RT, solids are filtered off from the mixture, and the filtrate is extracted by shaking with 3×200 ml of half-saturated sodium chloride solution and 2×200 ml of distilled water. After combining the organic phases, drying over sodium sulphate and evaporating to dryness, the residue is taken up in 50 ml of quinoline and the solution is stirred at 195–205° C. for 1 h. After cooling the solution, 400 ml of ethyl acetate are added and the quinoline is extracted by shaking with 4×200 ml of 2N hydrochloric acid. The organic phases are combined, dried over sodium sulphate and brought to dryness in a rotary evaporator. After column chromatography, a yield of 8.4 g of the title compound results as a red-brown oil. [TLC (petroleum ether/ethyl acetate, 6:4) $R_f$=0.65].

B6. 4-Methoxy-3-(2-oxocyclopentyloxy)bromobenzene 17.7 g (0.15 mol) of 2-chlorocyclopentanone and 41.4 g (0.3 ml) of potassium carbonate are added to a solution of 20 g (0.1 mol) of the compound prepared according to B7 in 300 ml of absolute DMF and the mixture is stirred at RT for 12 h. After filtering off the solids, the filtrate is concentrated, the residue is taken up in 500 ml of ethyl acetate and the solution is extracted by shaking with 3×200 ml of distilled water. Column chromatography affords 21.1 g of the title compound as a brown oil. [TLC (petroleum ether/ethyl acetate, 6:4) $R_f$=0.47].

B7. 3-Hydroxy-4-methoxybromobenzene

A suspension of 80 g (0.325 mol) of m-chloroperbenzoic acid in 500 ml of absolute methylene chloride is added dropwise over a period of 1 h to a suspension, cooled to 8° C., of 50.0 g (0.23 mol) of 5-bromo-2-methoxybenzaldehyde in 120 ml of methylene chloride, then the ice-cooling is removed and the mixture is allowed to come to RT. The mixture is snow-white after the dropwise addition and changes colour to yellow after 70 h. The reaction to give the corresponding ester can be monitored by means of TLC checking; TLC (petroleum ether/ethyl acetate, 6:4); $R_f$ (5-bromo-2-methoxybenzaldehyde)=0.71; $R_f$ (ester)=0.76. After stirring at RT for 70 h, the reaction to give the ester is quantitative according to TLC. The precipitate is filtered off from the solution, and the filtrate is washed with 5×200 ml of 5% strength sodium sulphite solution and 4×200 ml of half-saturated sodium hydrogen-carbonate solution, then treated with 50 ml of 2N sodium hydroxide solution and vigorously stirred for 30 min at RT. The organic phase is separated off from the basic phase and the sodium hydroxide phase is brought to pH 2 using half-concentrated hydrochloric acid. After extracting with 500 ml of ethyl acetate and drying the ethyl acetate phase over sodium sulphate, the organic phase is brought to dryness in a rotary evaporator. 45 g of the title compound are obtained as dark-red crystals of m.p. 45–46° C.

C1. 4-(2,3-Dihydro-7-methoxybenzofuran-2-spiro-1'-cyclopentan-4-yl)dibromomethylene-cyclohexane 4.6 g (0.018 mol) of triphenylphosphane are added under nitrogen to a solution of 2.6 g (7.8 mmol) of carbon tetrabromide in 20 ml of absolute methylene chloride and the mixture is stirred at RT for 15 min, during which the solution turns orange. After dropwise addition of 1.2 g (4 mmol) of the compound prepared according to B1 in 20 ml of absolute methylene chloride, the solution turns dark-red after ½ h. The organic phase is washed with saturated sodium chloride solution, dried over sodium sulphate and evaporated almost to dryness. 15 g of silica gel and 20 ml of a petroleum ether/ethyl acetate 8:2 mixture are added to the residue and the mixture is evaporated to dryness in a rotary evaporator. Column chromatography affords 1.3 g of the title compound as a brown oil. [TLC (petroleum ether/ethyl acetate; 8:2) $R_f$=0.74].

Commercial Utility

The compounds according to the invention have valuable pharmacological properties which make them commercially utilizable. As selective cyclic nucleotide phosphodiesterase (PDE) inhibitors (namely of type IV), they are suitable on the one hand as bronchial therapeutics (for the treatment of airway obstructions on account of their dilating and also on account of their respiratory rate- or respiratory drive-increasing action, but on the other hand especially for the treatment of disorders, in particular of inflammatory nature, e.g. of the airways (asthma prophylaxis), of the skin, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumour necrosis factor (TNF) or oxygen free radicals and proteases. In this connection, the compounds according to the invention are distinguished by low toxicity, good enteral absorption (high bioavailability), a great therapeutic breadth and the absence of significant side effects.

On account of the PDE-inhibiting properties, the compounds according to the invention can be employed in human and veterinary medicine as therapeutics, where they can be used, for example, for the treatment of prophylaxis of the following illnesses: acute and chronic (in particular inflammatory and allergen-induced) airway disorders of various origin (bronchitis, allergic bronchitis, bronchial asthma); dermatoses (especially of proliferative, inflammatory and allergic type) such as, for example, psoriasis (vulgaris), toxic and allergic contact eczema, atopic eczema, seborrhoeic eczema, lichen simplex, sunburn, pruritis in the anogenital region, alopecia areata, hypertrophic scars, discoid lupus erythematosus, follicular and widespread pyodermias, endogenous and exogenous acne, acne rosacea and also other proliferative, inflammatory and allergic skin disorders; disorders which are based on an excessive release of TNF and leukotrienes, e.g. disorders of the arthritic type (rheumatoid arthritis, rheumatoid spondylitis, osteoarthritis and other arthritic conditions), disorders of the immune system (AIDS, multiple schlerosis), types of shock [septic shock, endotoxin shock, gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the area of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and of the ureters in connection with kidney stones; or alternatively disorders of the CNS, such as, for example, depressions or arteriosclerotic dementia.

The invention furthermore relates to a method for the treatment of mammals, including humans, who are suffering form one of the abovementioned illnesses. The method is characterized in that a therapeutically active and pharmacologically tolerable amount of one or more of the compounds according to the invention is administered to the sick mammal.

The invention further relates to the compounds according to the invention for use in the treatment and/or prophylaxis of the illnesses mentioned.

The invention likewise relates to the use of the compounds according to the invention for the production of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention.

The medicaments are prepared by methods known per se and familiar to the person skilled in the art. As medicaments, the compounds according to the invention (=active compounds) are either employed as such, or preferably in combinations with suitable pharmaceutical auxiliaries, e.g. in the form of tablets, coated tablets, capsules, suppositories, patches, emulsions, suspensions, gels or solutions, the active compound content advantageously being between 0.1 and 95%.

The auxiliaries which are suitable for the desired pharmaceutical formulations are familiar to the person skilled in the art on account of his expert knowledge. Besides solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the compounds according to the invention are preferably also administered by inhalation. To do this, these are either administered directly as a powder (preferably in micronized form) or by atomizing solutions or suspensions which contain them. With respect to the preparation and administration forms, reference is made, for example, to the details in European Patent 0163965.

For the treatment of dermatoses, the compounds according to the invention are in particular used in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 0.5 mg/kg. The customary dose in the case of systemic therapy is between 0.05 and 2 mg/kg per day.

Biological Investigations

In the investigation of PDE IV inhibition at the cellular level, the activation of inflammatory cells has particular importance. As an example, FMLP (N-formulmethionylleucylphenylalanine)-induced superoxide production of neutrophilic granulocytes may be mentioned, which can be measured as luminol-potentiated chemoluminescence [Mc Phail L C, Strum S L, Leone P A and Sozzani S, The neutrophil respiratory burst mechanism. In "Immunology Series" 1992, 57, 47–76; ed. Coffey R G (Marcel Decker, Inc., New York-Basel-Hong Kong)].

Substances which inhibit chemoluminescence and also cytokine secretion and the secretion of proinflammatory mediators in inflammatory cells, in particular neutrophilic and eosinophilic granulocytes, are those which inhibit PDE IV. This isoenzyme of the phosphodiesterase families is particularly represented in granulocytes. Its inhibition leads to an increase in the intracellular cyclic AMP concentration and thus to the inhibition of cellular activation. PDE IV inhibition by the substances according to the invention is thus a central indicator for the suppression of inflammatory processes (Giembycz M A, Could isoenzyme-selective phosphodiesterase inhibitors render bronchodilatory therapy redundant in the treatment of bronchial asthma? Biochem Pharmacol 1992, 43, 2041–2051; Torphy T J et al., Phosphodiesterase inhibitors; new opportunities for treatment of asthma. Thorax 1991, 46, 512–523; Schudt C et al., Zardaverine: a cyclic AMP PDE III/IV inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and $Ca_i$. Naunyn-Schmiedebergs Arch Pharmacol 1991, 344, 682–690; Nielson C P et al., Effects of selective phosphodiesterase inhibitors on polymorphonuclear leukocyte respiratory burst. J. Allergy Clin Immunol 1990, 86, 801–808; Schade et al., The specific type III and IV phosphodiesterase inhibitor zardaverine suppress formation of tumor necrosis factor by macrophages. European Journal of Pharmacology 1993, 230, 9–14).

1. Inhibition of PDE IV Activity

Methodology

The activity test was carried out by the method of Bauer and Schwabe, which was adapted to microtitre plates (Naunyn-Schmiedebert's Arch. Pharmacol. 311, 193–198, 1980). In this test, the PDE reaction takes place in the first step. In a second step, the 5'-nucleotide formed is cleaved to give the uncharged nucleoside by a 5'-nucleotidase of the snake venom from *ophiophagus hannah* (king cobra). In the third step, the nucleoside is separated from the remaining charged substrate on ion exchange columns. Using 2 ml of 30 mM ammonium formate (pH 6.0), the columns are directly eluted into minivials to which is additionally added 2 ml of scintillator fluid for counting.

The inhibitory values determined for the compounds according to the invention follow from Table A below, in which the numbers of the compounds correspond to the numbers of the examples.

TABLE A

Inhibition of PDE IV activity

| Compound | -log $IC_{50}$ |
|---|---|
| 1 | 8.35 |
| 2 | 7.38 |
| 3 | 7.11 |

FORMULA SHEET I

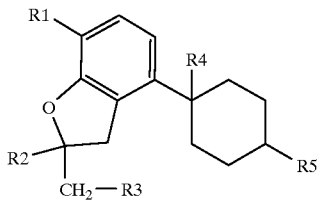
(I)

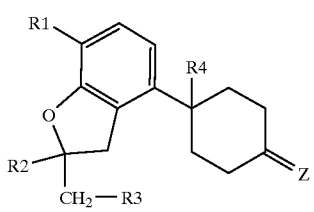
(II)

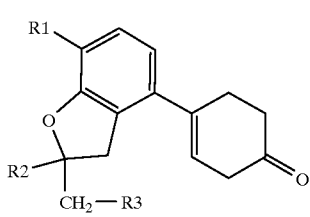
(III)

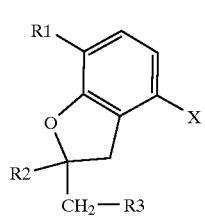
(IV)

FORMULA SHEET II

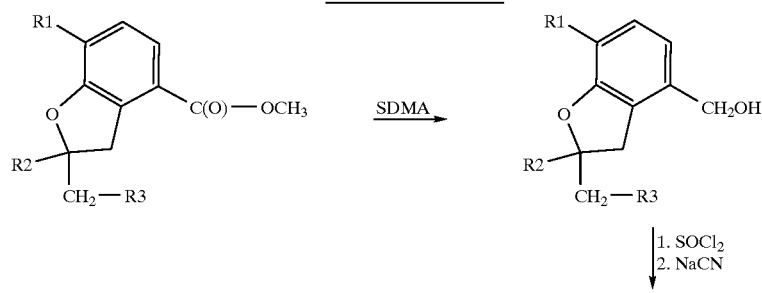

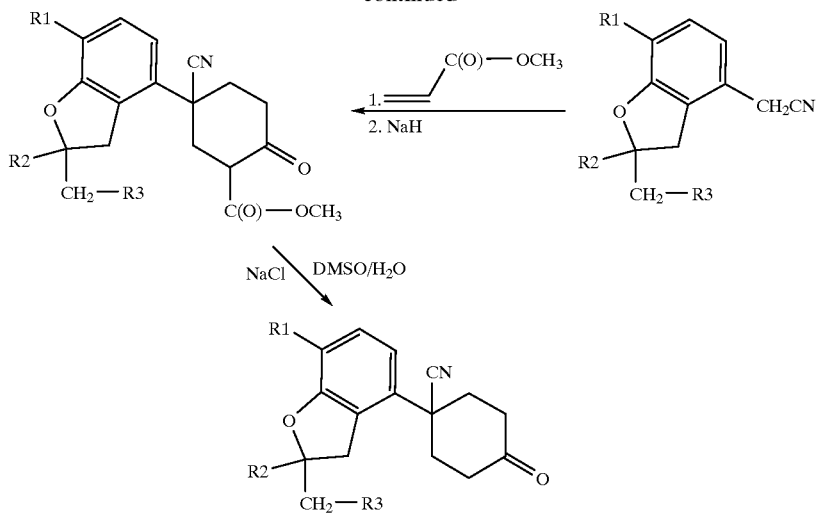

FORMULA SHEET IIa

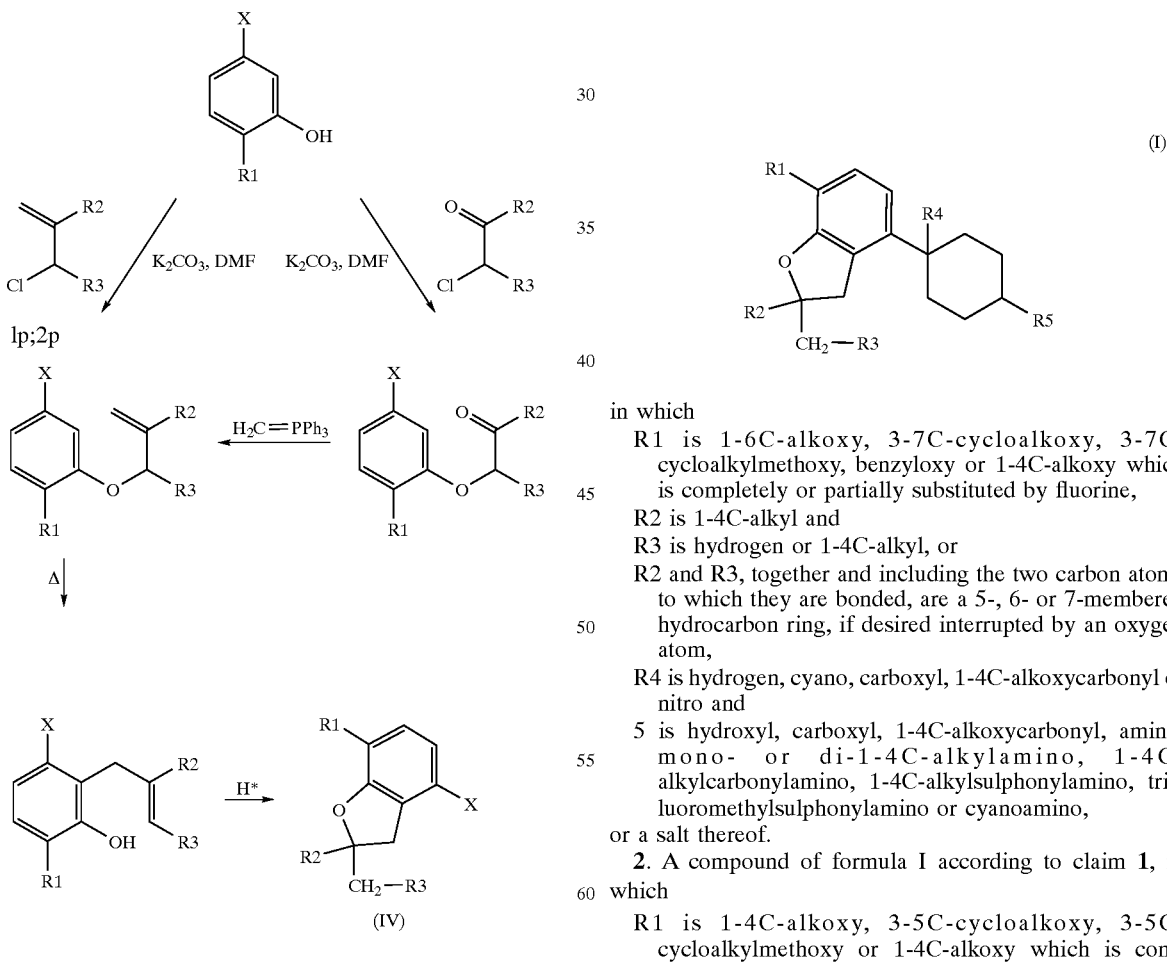

We claim:
1. A compound of formula I

(I)

in which
R1 is 1-6C-alkoxy, 3-7C-cycloalkoxy, 3-7C-cycloalkylmethoxy, benzyloxy or 1-4C-alkoxy which is completely or partially substituted by fluorine,
R2 is 1-4C-alkyl and
R3 is hydrogen or 1-4C-alkyl, or
R2 and R3, together and including the two carbon atoms to which they are bonded, are a 5-, 6- or 7-membered hydrocarbon ring, if desired interrupted by an oxygen atom,
R4 is hydrogen, cyano, carboxyl, 1-4C-alkoxycarbonyl or nitro and
5 is hydroxyl, carboxyl, 1-4C-alkoxycarbonyl, amino, mono- or di-1-4C-alkylamino, 1-4C-alkylcarbonylamino, 1-4C-alkylsulphonylamino, trifluoromethylsulphonylamino or cyanoamino,
or a salt thereof.
2. A compound of formula I according to claim 1, in which
R1 is 1-4C-alkoxy, 3-5C-cycloalkoxy, 3-5C-cycloalkylmethoxy or 1-4C-alkoxy which is completely or partially substituted by fluorine,
R2 is 1-4C-alkyl and
R3 is hydrogen or 1-4C-alkyl, or R2 and R3, together and including the two carbon atoms to which they are bonded, are a cyclopentane, cyclohexane, tetrahydrofuran or tetrahydropyran ring, R4 is hydrogen, cyano, carboxyl or 1-2C-alkoxycarbonyl and R5 is hydroxy, carboxyl, 1-2C-alkoxycarbonyl, amino or mono- or di-1-2C-alkylamino, or a salt thereof.

3. A compound of formula I according to claim 1, in which

R1 is 1-4C-alkoxy, 3-5C-cycloalkoxy or 1-4C-alkoxy which is completely or partially substituted by fluorine, R2 and R3, together and including the two carbon atoms to which they are bonded, are a cyclopentane or cyclohexane ring, R4 is hydrogen, cyano, carboxy or 1-2C-alkoxycarbonyl and R5 is hydroxy, carboxyl, 1-2C-alkoxycarbonyl, amino or mono- or di-1-2C-alkylamino, or a salt thereof.

4. A compound of formula I according to claim 1, in which

R1 is methoxy,

R2 and R3, together and including the two carbon atoms to which they are bonded, are a cyclopentane ring, R4 is hydrogen or cyano and R5 is hydroxyl or carboxyl, or a salt thereof.

5. Process for the preparation of the compounds of the formula I according to claim 1 and their salts, characterized in that a) compounds of the formula II

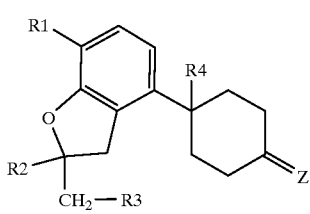

(II)

in which R1, R2, R3 and R4 have the meanings indicated in claim 1 and Z is an oxygen atom (O) are reacted under conditions which, if desired, selectively reduce the carbonyl group or in that b) for the preparation of compounds of the formula I in which R1, R2, R3 and R4 have the meanings indicated in claim 1 and R5 is a carboxyl group, corresponding compounds of the formula II in which Z is the group $C(Br)_2$ are hydrolysed and in that, if desired, compounds of the formula I obtained are then converted into their salts, or in that salts of the compounds of the formula I obtained are converted into the free compounds.

6. A medicament composition comprising a suitable pharmaceutical auxiliary and/or excipient and an effective amount of a compound of claim 1 or of a pharmacologically-acceptable salt thereof.

7. A method for treating a susceptible illness which comprises administering an effective amount of a compound of claim 1 or of a pharmacologically-acceptable salt thereof to a patient afflicted with such illness.

8. A method of compounding a medicament composition which comprises admixing a suitable auxiliary or excipient with an effective amount of a compound of claim 1 or of a pharmacologically-acceptable salt thereof.

9. In a method for compounding a pharmaceutical composition which comprises admixing an effective amount of a nucleotide phosphodiesterase (PDE) inhibitor with a suitable pharmaceutical auxiliary or excipient, the improvement wherein the nucleotide phosphodiesterase inhibitor is a compound of claim 1 or a pharmaceutically-acceptable salt thereof.

10. A method of claim 9 for producing a medicament composition for treating an airway disorder.

11. A method according to claim 9 for producing a medicament composition for treating a dermatosis.

12. A method for treating a disorder susceptible to treatment with a cyclic nucleotide phosphodiesterase (PDE) inhibitor which comprises administering an effective amount of a compound of claim 1 or of a pharmacologically-acceptable salt thereof to a patient afflicted with such disorder.

* * * * *